United States Patent
Viola

(10) Patent No.: US 9,986,985 B2
(45) Date of Patent: Jun. 5, 2018

(54) ARTICULATING JOINT FOR SURGICAL INSTRUMENTS

(71) Applicant: Covidien LP, Mansfield, MA (US)

(72) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 762 days.

(21) Appl. No.: 14/025,860

(22) Filed: Sep. 13, 2013

(65) Prior Publication Data

US 2014/0018826 A1 Jan. 16, 2014

Related U.S. Application Data

(63) Continuation of application No. 11/900,485, filed on Sep. 11, 2007, now Pat. No. 8,556,151.

(51) Int. Cl.
| | | |
|---|---|---|
| *A61B 17/00* | (2006.01) | |
| *A61B 17/072* | (2006.01) | |
| *A61B 17/068* | (2006.01) | |
| *A61B 17/10* | (2006.01) | |
| *A61B 17/29* | (2006.01) | |

(52) U.S. Cl.
CPC ...... *A61B 17/00234* (2013.01); *A61B 17/068* (2013.01); *A61B 17/072* (2013.01); *A61B 17/10* (2013.01); *A61B 2017/003* (2013.01); *A61B 2017/2903* (2013.01); *A61B 2017/2927* (2013.01)

(58) Field of Classification Search
CPC ...... A61B 17/00234; A61B 2007/0069; A61B 17/068; A61B 17/000234
USPC ...................... 606/142; 227/175.1
See application file for complete search history.

(56) References Cited

U.S. PATENT DOCUMENTS

| | | |
|---|---|---|
| 5,312,023 A | 5/1994 | Green et al. |
| 5,381,943 A | 1/1995 | Allen et al. |
| 5,431,323 A | 7/1995 | Smith et al. |
| 5,456,401 A | 10/1995 | Green et al. |
| 5,485,952 A | 1/1996 | Fontayne |
| 5,540,375 A | 7/1996 | Bolanos et al. |
| 5,575,799 A | 11/1996 | Bolanos et al. |
| 5,601,224 A | 2/1997 | Bishop |
| 5,607,095 A | 3/1997 | Smith et al. |

(Continued)

FOREIGN PATENT DOCUMENTS

EP 1 813 207 8/2007

OTHER PUBLICATIONS

European Search Report EP 08252971.0-1265 dated Nov. 20, 2008.

*Primary Examiner* — Hemant M Desai
*Assistant Examiner* — Eduardo R Ferrero

(57) ABSTRACT

A surgical apparatus is disclosed. An actuation mechanism is operable from a proximal portion of the surgical apparatus and a tool assembly is pivotally positioned on a distal portion of the surgical apparatus. The tool assembly is movable between a first position in which the tool assembly is substantially aligned with a longitudinal axis of the surgical apparatus, and a second position in which the tool assembly is pivoted away from the longitudinal axis of the surgical apparatus. An articulation mechanism is positionable to move the tool assembly between the first and second positions. A drive mechanism includes a first shaft operably engaged with a second shaft at an articulation joint. The drive mechanism is configured to transfer rotational motion from the first shaft to the second shaft.

21 Claims, 10 Drawing Sheets

(56) References Cited

U.S. PATENT DOCUMENTS

| | | |
|---|---|---|
| 5,673,840 A | 10/1997 | Schulze et al. |
| 5,690,269 A | 11/1997 | Bolanos et al. |
| 5,704,534 A | 1/1998 | Huitema et al. |
| 5,713,505 A | 2/1998 | Huitema |
| 5,725,536 A | 3/1998 | Oberlin et al. |
| 5,797,956 A * | 8/1998 | Furnish ............... A61B 17/2909 |
| | | 606/174 |
| 5,810,716 A * | 9/1998 | Mukherjee ............... B25J 9/102 |
| | | 600/139 |
| 5,820,009 A | 10/1998 | Melling et al. |
| 5,823,066 A | 10/1998 | Huitema et al. |
| 5,901,895 A | 5/1999 | Heaton et al. |
| 6,010,054 A | 1/2000 | Johnson et al. |
| 6,241,139 B1 * | 6/2001 | Milliman ......... A61B 17/07207 |
| | | 227/175.1 |
| 6,447,527 B1 * | 9/2002 | Thompson ......... A61B 17/3494 |
| | | 606/174 |
| 6,663,641 B1 | 12/2003 | Kovac et al. |
| 6,786,382 B1 | 8/2004 | Hoffman |
| 6,877,647 B2 | 4/2005 | Green et al. |
| 7,055,731 B2 | 6/2006 | Shelton et al. |
| 7,111,769 B2 | 9/2006 | Wales et al. |
| 7,246,734 B2 | 7/2007 | Shelton, IV |
| 7,404,508 B2 | 7/2008 | Smith et al. |
| 7,410,086 B2 | 8/2008 | Ortiz et al. |
| 7,416,101 B2 | 8/2008 | Shelton et al. |
| 7,549,998 B2 * | 6/2009 | Braun ..................... A61B 17/29 |
| | | 606/205 |
| 7,674,269 B2 * | 3/2010 | Hoffman ............ A61B 17/0401 |
| | | 606/104 |
| 7,753,258 B1 | 7/2010 | Viola |
| 7,798,386 B2 * | 9/2010 | Schall ............. A61B 17/07207 |
| | | 227/175.1 |
| 8,241,322 B2 | 8/2012 | Whitman et al. |
| 2005/0006431 A1 | 1/2005 | Shelton et al. |
| 2005/0006432 A1* | 1/2005 | Racenet ........... A61B 17/07207 |
| | | 227/176.1 |
| 2005/0096694 A1 | 5/2005 | Lee |
| 2005/0273084 A1 | 12/2005 | Hinman et al. |
| 2005/0279804 A1 | 12/2005 | Scirica et al. |
| 2006/0011699 A1 | 1/2006 | Olson et al. |
| 2006/0016853 A1 | 1/2006 | Racenet |
| 2006/0025817 A1 | 2/2006 | Ortiz et al. |
| 2006/0047308 A1 | 3/2006 | Ortiz et al. |
| 2006/0049229 A1 | 3/2006 | Milliman et al. |
| 2007/0023477 A1 | 2/2007 | Whitman et al. |
| 2007/0027469 A1 * | 2/2007 | Smith ............... A61B 17/07207 |
| | | 606/205 |
| 2009/0095790 A1 * | 4/2009 | Whitman ......... A61B 17/07207 |
| | | 227/175.1 |

\* cited by examiner

ARTICULATING JOINT FOR SURGICAL INSTRUMENTS

CROSS-REFERENCE TO RELATED APPLICATIONS

This application is a continuation of U.S. application Ser. No. 11/900,485 filed Sep. 11, 2007, and the disclosures of each of the above-identified applications are hereby incorporated by reference in their entirety.

BACKGROUND

Technical Field

The present disclosure relates to surgical instruments and, more particularly, to surgical instruments for use in laparoscopic and endoscopic procedures having an articulating joint.

Background of Related Art

Laparoscopic and endoscopic surgical procedures are minimally invasive procedures in which operations are carried out within the body by means of elongated instruments inserted through small entrance openings in the body. In minimally invasive procedures, the initial opening in the body tissue to allow passage of instruments to the interior of the body may be a natural passageway of the body (e.g. mouth or anus) or it can be created by a tissue piercing instrument such as a trocar. With the aid of a cannula assembly inserted into the opening, laparoscopic or endoscopic instrumentation may then be used to perform desired surgical procedures.

Because endoscopic and laparoscopic tubes, instrumentation, and any required punctures or incisions are relatively narrow, endoscopic and laparoscopic surgery is less invasive and causes much less trauma to the patient as compared to procedures in which the surgeon is required to cut open large areas of body tissue. Laparoscopic and endoscopic procedures often require the surgeon to operate on organs, tissues, and vessels far removed from the incision. Thus, instruments used in these procedures are long and narrow, and must be functionally controllable from one end thereof. Mechanical actuation of such instruments is generally constrained to the movement of the various components along a longitudinal axis formed by the endoscopic portion instrument.

Conventional laparoscopic and endoscopic instruments include a handle assembly, an elongated member extending from the handle assembly and a tool assembly mounted on the distal end of the elongated member. The tool assembly may form graspers, forceps, vessel sealers, surgical staplers, clip appliers and the like. The handle assembly may be configured with a trigger for manual actuation of the tool assembly or may include a powered actuation assembly. Depending on the design of the instrument, actuation of the handle assembly may either cause a rod to longitudinally traverse the elongated member thereby actuating the tool assembly mounted on the distal end. Alternatively, the actuation of the handle assembly may cause rotation of a drive shaft extending the length of the elongated member. Both methods of transferring the actuation force from the handle assembly to the tool assembly are known in the art.

Commonly owned U.S. Pat. No. 5,653,374 to Young et al., the disclosure of which is hereby incorporated by reference herein in its entirety, discloses a surgical stapler for use in endoscope procedures that utilizes a rotating drive shaft to transfer the actuation force from the handle assembly to the tool assembly, in this case, a stapler. Actuation of the motorized handle assembly causes the rotation of the drive shaft within the elongated body member. The drive shaft is configured such that rotation of the shaft causes actuation of the stapling assembly located on the distal end of the elongated body member.

Commonly owned U.S. Pat. No. 5,830,221 to Stein et al., the disclosure of which is hereby incorporated by reference herein in its entirety, discloses an endoscopic instrument for applying fasteners having a trigger for manual actuation of the handle assembly. Squeezing of the trigger causes rotational motion of a drive shaft which in turn actuates the tool assembly, a fastener dispensing distal end.

Endoscopic and laparoscopic procedures are performed on tissue within the body cavity that may be difficult to access. Whether obstructed by bone, organs and other tissue, or simply the configuration of the body cavity, accessing tissue using conventional endoscopic or laparoscopic instruments can be challenging. Manipulating a tool assembly located on the distal end of a rigid shaft can prove challenging. To address this problem and overcome the inability to access difficult to reach tissue, endoscopic and laparoscopic instruments have been developed with an articulating joint which enables a tool assembly mounted on the distal end of an elongated member to be articulated. Commonly owned U.S. Pat. No. 5,690,269 to Bolanos et al., incorporated by reference herein in its entirety, discloses an endoscopic stapler having an articulating stapling assembly.

Therefore, it would be beneficial to have an endoscopic surgical instrument including an articulating joint for articulating a tool assembly mounted on the distal end thereof.

BRIEF DESCRIPTION OF THE DRAWINGS

Embodiments of the presently disclosed surgical instrument having an articulating joint are described herein with reference to the drawings, wherein.

DETAILED DESCRIPTION OF THE EMBODIMENTS

Figure 1:
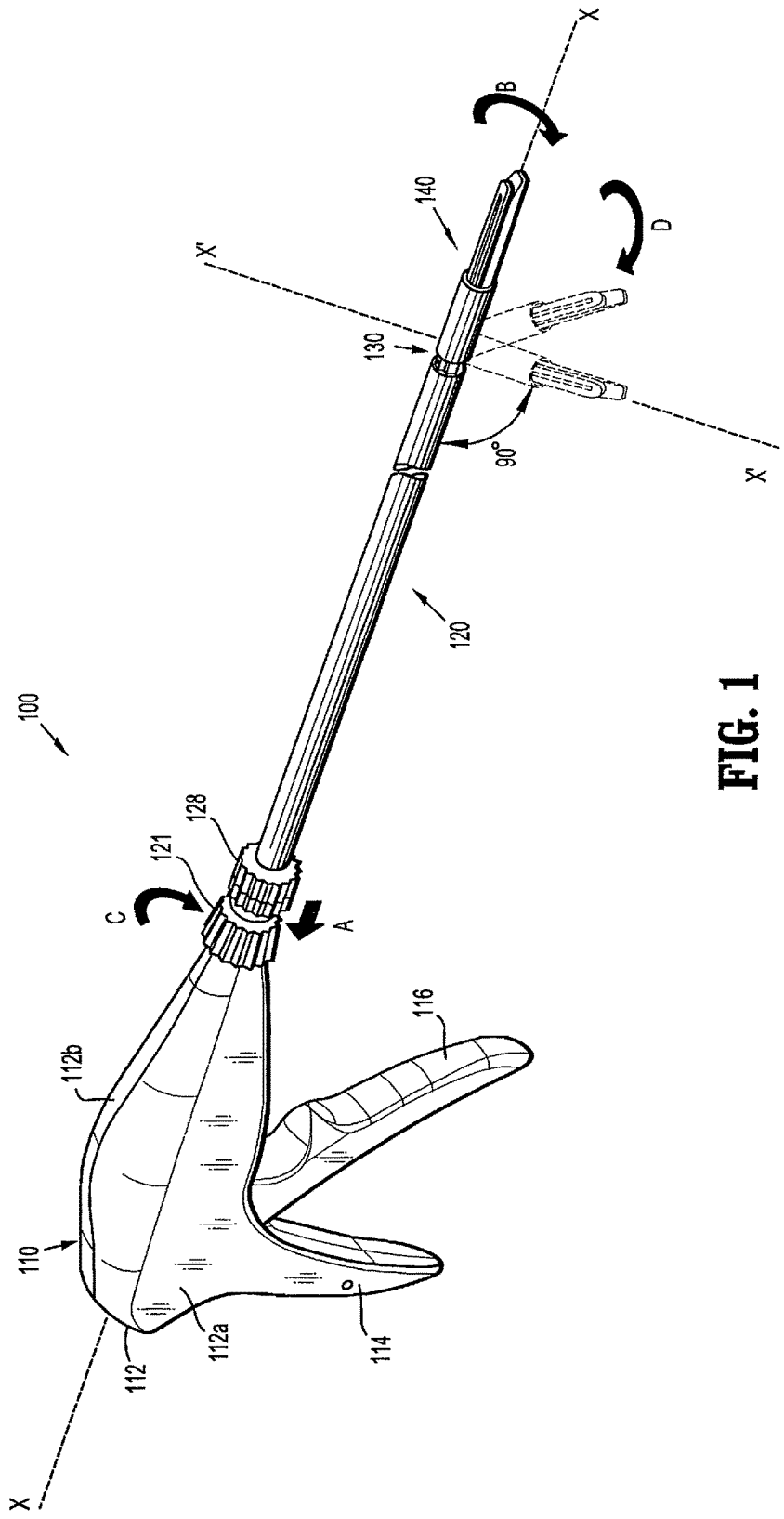
FIG. 1 is a perspective view of a surgical instrument according to an embodiment of the present disclosure.

Embodiments of the presently disclosed surgical instrument will now be described in detail with reference to the drawings, in which like reference numerals designate identical or corresponding elements in each of the several views. As used herein, the term "distal" refers to that portion of the instrument, or component thereof which is further from the user while the term "proximal" refers to that portion of the instrument or component thereof which is closer to the user.

The articulation mechanism of the present disclosure may be incorporated into any number of surgical devices including but not limited to clip appliers, vessel sealers, forceps/graspers, cutting tools, surgical staplers or fasteners, and the like. To better understand the operation of the present embodiments, this disclosure will describe the articulation mechanism as it relates to a surgical apparatus for applying surgical staples or a surgical stapler. It is understood that reference to a surgical stapler is by no means limiting and that the embodiments of the present disclosure may be incorporated into clip appliers, vessel sealers, forceps/graspers, cutting tools, and the like.

The presently disclosed surgical apparatus is illustrated in FIGS. 1-7B and is shown generally as surgical stapler 100. Surgical stapler 100 includes a handle assembly 110, an endoscopic portion 120 and a tool assembly 140. Endoscopic portion 120 extends from handle assembly 110 and includes an articulation joint 130. Tool assembly 140 is operably connected to the distal end of endoscopic portion 120. Handle assembly 110 functions to open and close tool assembly 140. As shown by arrows A-D, and as will be described in further detail below, endoscopic portion 120 may be articulated at articulation joint 130 (arrow D) by manipulating an articulation knob 128 along endoscopic portion 120 in the direction of arrow A. Endoscopic portion 120 may also be rotated around axis X-X relative to handle assembly 110 (arrow B) by manipulating a rotation knob 121 in the direction of arrow C.

Handle assembly 110 is configured for operable engagement by a user, preferably with a single hand. Handle assembly 110 includes a housing 112 which may be formed as two separate housings 112a, 112b. Handle assembly 110 further includes a fixed handle portion 114 extending from housing 112. A trigger 116 is pivotally mounted to housing 112. Squeezing of trigger 116 towards fixed handle portion 114 operates to turn a drive shaft 65 (FIG. 2) in a first direction, thereby actuating tool assembly 140 positioned at the distal end of articulating shaft 120, as will be described in further detail below. Release of trigger 116 operates to turn drive shaft 65 in an opposite or second direction, thereby reversing or deactuating tool assembly 140.

Figure 2:
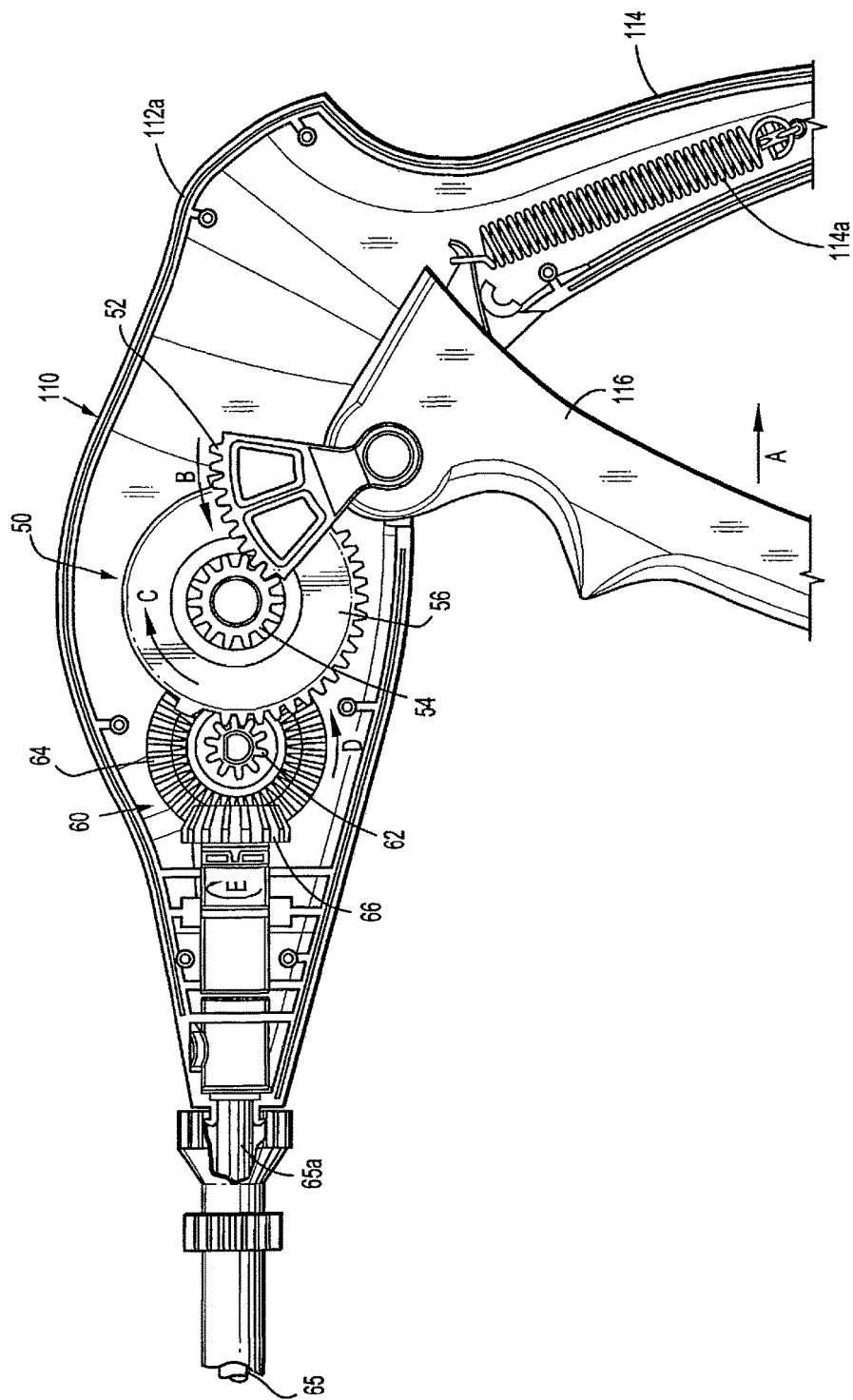
FIG. 2 is a cross-sectional side view of the handle assembly of the surgical instrument of FIG. 1.

Now referring to FIG. 2, hand assembly 110 further includes a coupling mechanism 50 and a drive assembly 60. Coupling mechanism 50 includes a gear member 52 operably connected to trigger 116, a trigger gear 54 operably engaged with gear member 52 and an idler gear 56. Drive assembly 60 operably couples coupling mechanism 50 and drive shaft 65. Drive assembly 60 is configured to convert the longitudinal motion created by the squeezing of trigger 116 and the actuation of coupling mechanism 50 into a rotational motion of drive shaft 65. Drive assembly 60 includes a drive gear 62, a first beveled gear 64, and a second beveled gear 66. Drive gear 62 of drive assembly 60 engages idler gear 56 of coupling mechanism 50. Rotation of drive gear 62 causes rotation of first beveled gear 64. First beveled gear 64 is configured to engage second beveled gear 66. As shown, second beveled gear 66 is oriented perpendicularly to first beveled gear 64. Thus, second beveled gear 66 rotates around longitudinal axis X-X.

In operation, trigger 116 is squeezed towards fixed handle portion 114 (arrow A) causing gear portion 52 to move relative to trigger gear 54. Movement of gear portion 52 (arrow B) causes engagement with trigger gear 54, thereby rotating trigger gear 54 and attached idler gear 56 in a first or clockwise longitudinal direction (arrow C). Engagement of drive gear 62 with idler gear 56 causes rotation of drive gear 62 and attached first beveled gear 64 in a second or counterclockwise longitudinal direction (arrow D). Rotation of first beveled gear 64 causes rotation of second beveled gear 66 in a first clockwise axial direction (arrow E), thereby causing rotation of drive shaft 65 in a first axial direction. A spring 114a mounted within fixed handle 114 is configured to bias trigger 116 to its original position upon thereof.

Release of trigger 116 causes rotation of trigger gear 54 and attached idler gear 56 in a second counterclockwise direction. Rotation of idler gear 56 in the second direction causes rotation of drive gear 62 and first beveled gear 64 in the first or clockwise direction. Rotation of first beveled gear 64 causes rotation of second beveled gear 66 and connected drive shaft 65 in a second counterclockwise axial direction. By varying the configuration of trigger 116 and the length of gear portion 52 the amount of rotation of drive shaft 65 may be controlled. The rotation of drive shaft 65 may also be affected by varying the size of the gears disposed between trigger 116 and drive shaft 65. Depending on the configuration of tool assembly 140, e.g. forceps, grasper, stapler, clip applier, drive shaft 65 may be rotated more or less per squeeze of trigger 116. In an alternate embodiment, coupling mechanism 50 may be configured to prevent rotation of drive shaft 65. In this manner, coupling mechanism 50 may include a pawl or lever for locking trigger 116 in position at various stages of actuation, and thus prevent rotation of drive shaft 65. Gear portion 52 may be configured as a pawl for engaging and disengaging trigger gear 54 at different stages.

As noted above, handle assemblies that produce a rotation drive shaft are known in the art, and the aspects of the present disclosure are not limited to the above described manual pistol grip instrument. Commonly owned U.S. Pat. No. 5,653,374 to Young et al. discloses surgical stapler having a motorized handle assembly. It is envisioned that the aspects of the present disclosed articulation mechanism may be incorporated into any handle assembly which relies on rotation of a drive shaft for actuation of a tool assembly.

Figure 3:
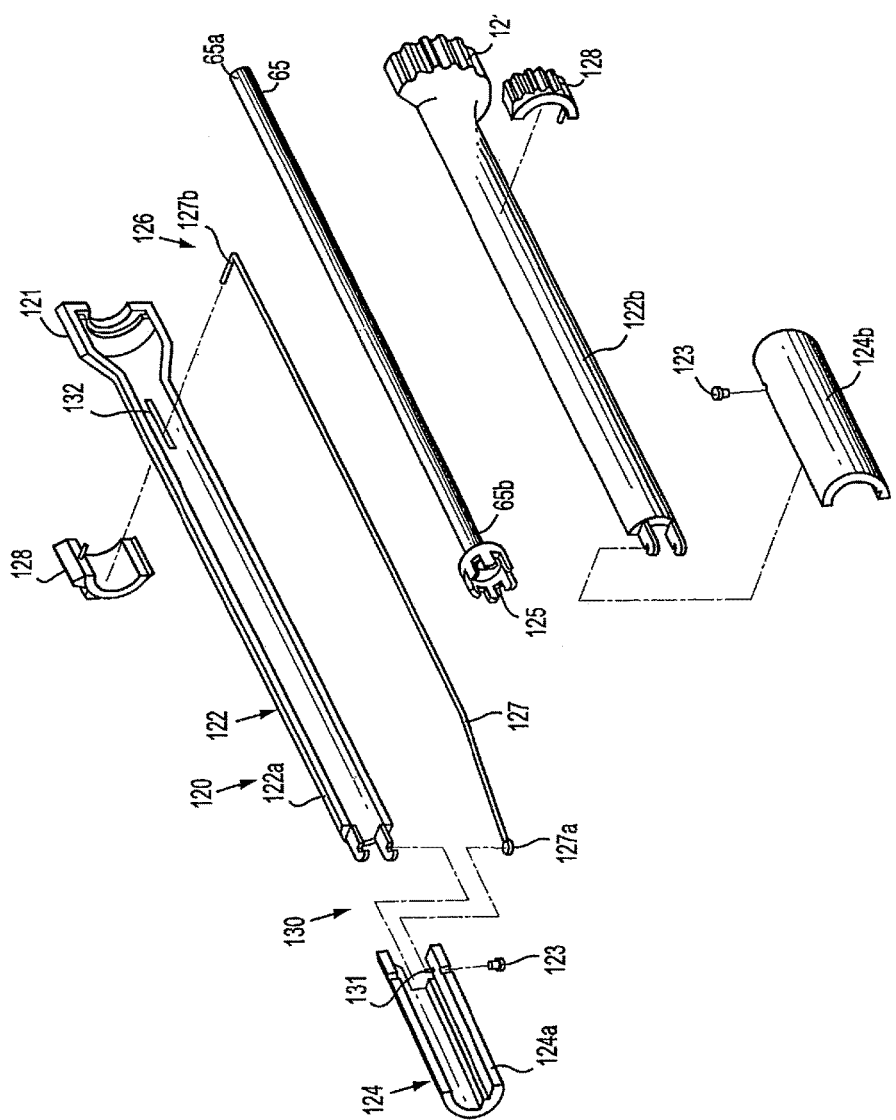
FIG. 3 is an exploded perspective view of the endoscopic portion of the surgical instrument of FIG. 1.
Figure 4:
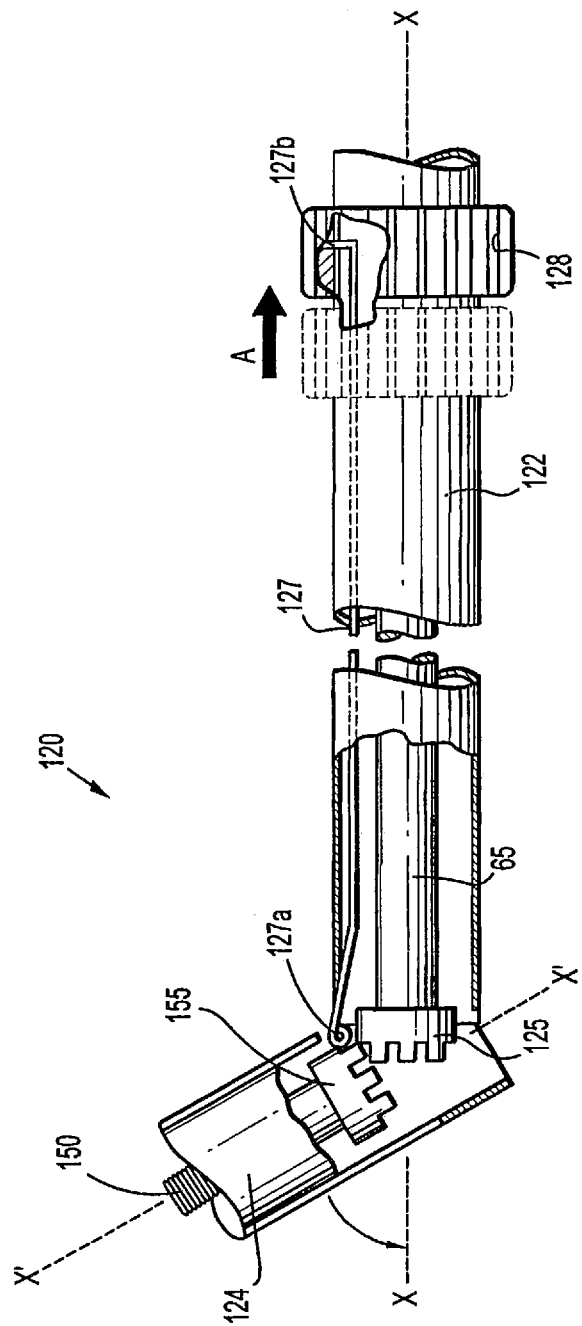
FIG. 4 is a partial cut away top view of the endoscopic portion of the surgical instrument of FIG. 1.

Referring now to FIGS. 3 and 4, endoscopic portion 120 is configured and dimensioned to be inserted into and through a cannula or other narrow opening. Endoscopic portion 120 includes an elongated portion 122, an articulation portion 124, articulation joint 130 located therebetween, and an articulation mechanism 126 for effecting articulation at articulation joint 130. Articulation joint 130 is configured for manipulating tool assembly 140 (FIGS. 6A-6C) mounted on the distal end of articulation portion 124. Elongated portion 122 includes first and second elongated members 122a, 122b. Rotation knob 121 is formed at a proximal end of elongated portion 122 and is configured for rotatable engagement with handle assembly 110. Rotation knob 121 may be knurled, grooved, or have other outer surface to configurations facilitate grasping thereof. Rotation knob 121 permits a surgeon to rotate endoscopic portion 120 and tool assembly 140 relative to handle assembly 110. Articulation portion 124 includes first and second articulation members 124a, 124b. Elongated portion 122 is pivotally connected to articulation portion 124 by pivot pins 123.

Articulation mechanism 126 permits the articulation of articulation portion 124 relative to elongated portion 122 at articulation joint 130. Articulation mechanism 126 includes an articulation rod 127 and an articulation knob 128. Articulation rod 127 includes a first distal end 127a forming a loop for engaging a pin 131 formed on articulation portion 124. Articulation rod 127 extends from articulation portion 124, through articulation joint 130 and into elongated member 122. Articulation rod 127 terminates in a hook 127b. Hook 127b extends through a slot 132 formed in first elongated member 122a and engages articulation knob 128. Articulation knob 128 is slidably mounted about elongated member 122. Proximal movement of articulation knob 128 causes articulation portion 124 of endoscopic portion 120 and tool assembly 140, shown in phantom (FIG. 1), to deflect at articulation joint 130 away from central axis X-X (arrows A and D). Frictional engagement of articulation knob 128 with elongated portion 122 prevents articulation joint 130 from over articulating or straightening out. Arrows C and B depict rotational movement of endoscopic portion 120 and distal portions of surgical stapler 100 which can be achieved by rotating rotation knob 121.

Referring now to FIG. 4, articulation is achieved by pulling articulating knob 128 in a proximal direction (arrow A). This proximal movement causes articulating rod 127 to pull on articulation joint 130 at pin 131. When articulated, axis X'-X' of tool assembly 140 and articulation joint 130 moves away from axis X-X formed by non-articulating endoscopic portion 120. Tool assembly 140 of surgical stapler 100 may be articulated such that stapling occurs along axis X'-X'. Surgical stapler 100 may be configured such that elongated portion 122 and articulation portion 124 move relative to one another in discrete stops of angular position. Elongated portion 122 may include grooves or indents that enable articulation knob 128 to be selectively positioned about elongated portion 122, thereby selectively position articulation portion 124 at discrete angles relative to elongated portion 122. Surgical stapler 100 may instead be configured to allow continuous variable angles between elongated portion 122 and articulating portion 124 ranging from about 0° to about 90°.

Drive shaft 65 is rotatably mounted within elongated portion 122. Proximal end 65a of drive shaft 65 is operably connected to second beveled gear 66 located within handle assembly 110 (FIG. 2). Rotation of second beveled gear 66 causes rotation of drive shaft 65. Distal end 65b of drive shaft 65 (FIG. 3) includes a first articulation gear 125. Drive shaft 65 may include an extension mechanism 166 (FIGS. 5B and 5C) configured for adjusting the length of drive shaft 65 during articulation of articulation mechanism 130. As will be described below, articulation portion 124 and tool assembly 140 include a drive screw 150 rotatably mounted therein. Drive screw 150 includes a second articulation gear 155 formed on the proximal end thereof. First and second articulation gears 125, 155 have a plurality of teeth in a circular or semi-circular arrangement and may have a castle-turret-like shape. However, it is envisioned that any gear configuration capable of remaining engaged through a 90° articulation has been contemplated by this disclosure. Each of first and second articulation gears 125, 155 include a plurality of rounded teeth 125a, 155a, respectively, configured to engage one another through a 90° articulation of articulating portion 124.

Figure 5A:
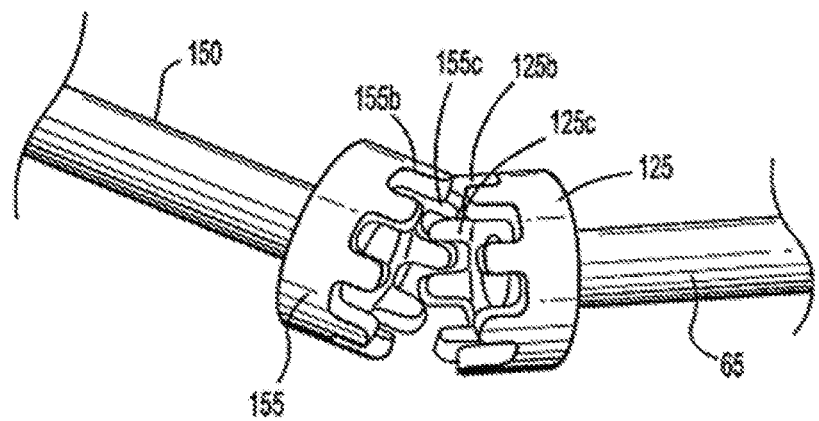
FIG. 5A is an enlarged perspective view of the articulation gears of the instrument of FIG. 4.
Figure 5B:
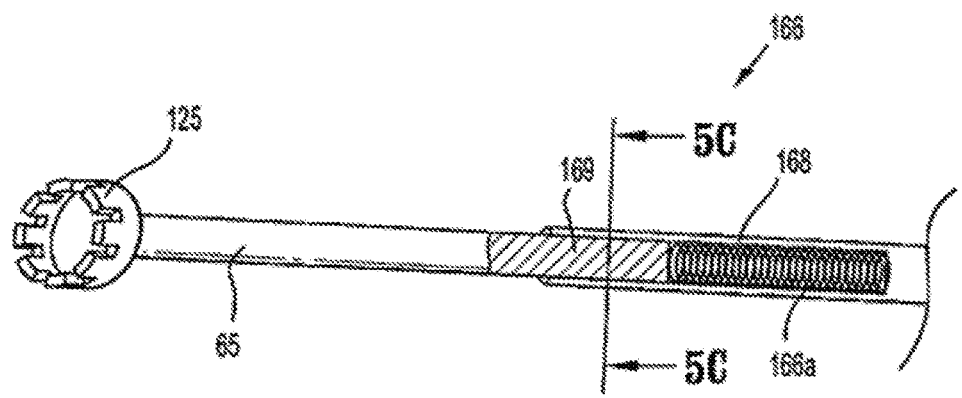
FIG. 5B is an enlarged partial cross-sectional side view of the drive shaft of the instrument of FIG. 4.
Figure 5C:
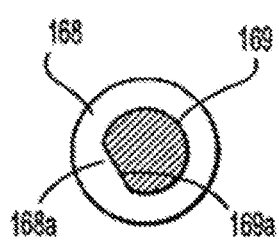
FIG. 5C is a cross-sectional end view of the drive shaft of FIG. 5B taken along section line 5C-5C.

When elongated portion 122 and articulation portion 124 are aligned, teeth 125a of first articulation gear 125 completely engage teeth 155a of second articulation gear 155. Squeezing of trigger 116 causes axial rotation of shaft 65 as described above. Axial rotation of shaft 65, and thus articulating gear 125 mounted thereon, along axis X-X, causes axial rotation of second articulation gear 155, and, thus, rotation of screw drive 150, also along axis X-X. As endoscopic portion 120 is articulated, first and second articulation gears 125, 155 move angularly relative to one another, and fewer of teeth 125a, 125b remain engaged (FIG. 5A). At 90° of articulation between elongated portion 122 and articulating portion 124, first and second articulation gears 125, 155 and, thus teeth 125a, 155b, are perpendicular to one another.

At complete articulation, rotation of articulating gear 125 in a first counter-clockwise direction cause rotation of second articulation gear 155 in a second counter-clockwise direction. One complete rotation of first articulation gear 125 causes one complete rotation of second articulation gear 155. In this configuration as few as one tooth 125a, 155a on each first and second articulation gears 125, 155, respectively, may be engaged at one time. As first articulation gear 125 rotates the number of teeth 125a thereon engaged with teeth 155a of second articulation 155 remains constant, while the particular teeth 125a, 155a that are actually engaged changes. As one of teeth 155a disengages from one of teeth 125a a second of teeth 155a is engaged to a second of teeth 125a. One complete rotation of first and second articulation gears 125, 155 will cause the engagement and disengagement of each of teeth 125a, 155a.

By including an extension mechanism 166 in drive shaft 65, the length of drive shaft 65 may be extended or contracted as necessary to accommodate the articulation of articulation joint 130 and to ensure first articulation gear 125 remains engaged with second articulation gear 155 throughout articulation. In this manner, at least one tooth of teeth 125a formed on first articulation gear 125 may remain fully engaged with at least one tooth of teeth 155a.

Extension mechanism 166 includes a receiving end 168, an insertion end 169 and spring 166a. Receiving end 168 is slideably received within insertion end 169. Receiving end 169 may include tab or raised portion 169a for engagement with a notch or groove 168a of insertion end 168. Spring 166a is positioned between the proximal end of insertion end 169 and an inner end surface of receiving end 168. Spring 166a is configured such that when endoscopic portion 120 of surgical stapler 100 is in a first or aligned position, spring 166a is slightly biased. In this manner, release of pressure on distal end of drive shaft 65 causes extension mechanism 166 to extend.

In the present embodiment, tool assembly 140 comprises a stapling assembly. As discussed above, the aspects of the present disclosure can be incorporated into any tool assembly that can be actuated by rotational motion of a drive shaft. Tool assembly 140 may instead comprise a clip applier, graspers and forceps, vessel sealer, or the like.

Figure 6:
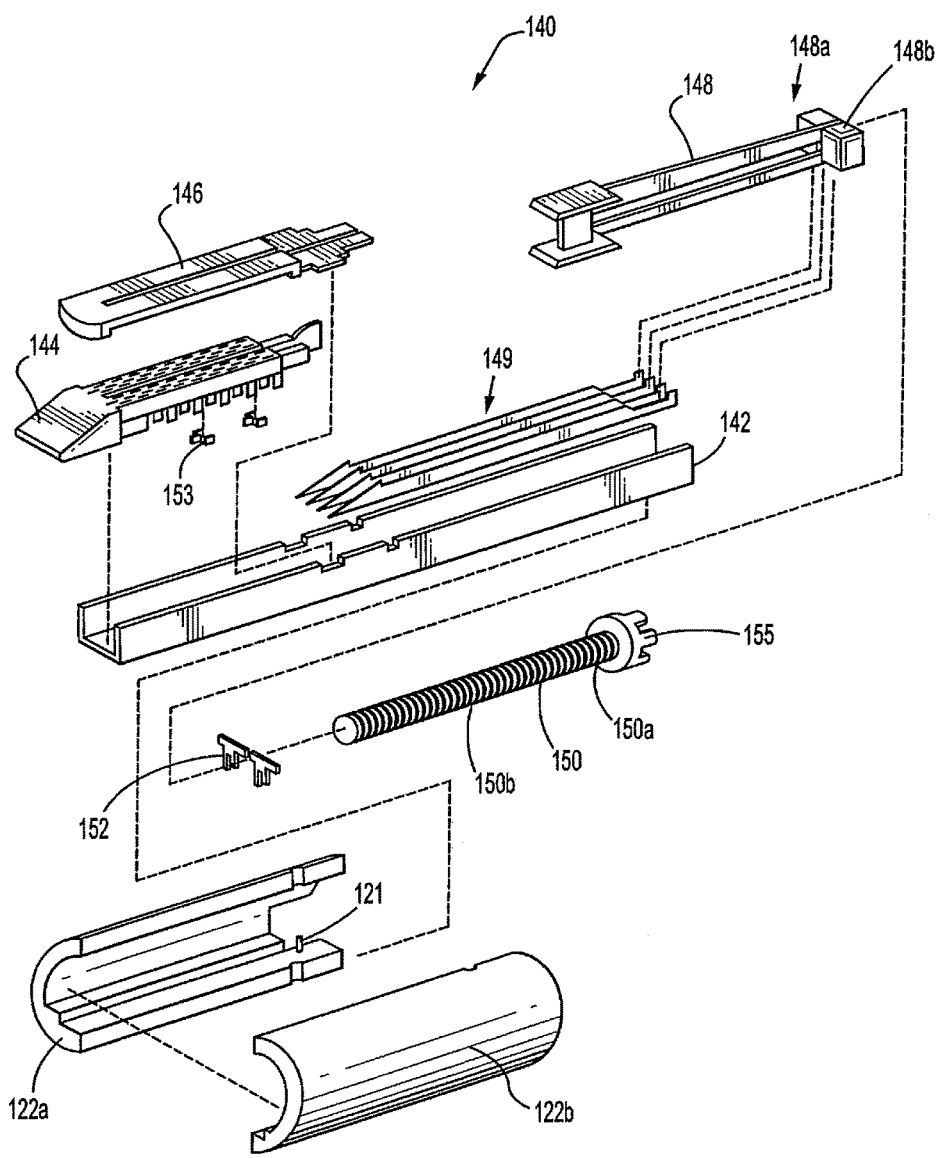
FIG. 6 is an exploded perspective view of the stapling assembly of the surgical instrument of FIG. 1.
Figure 7A:
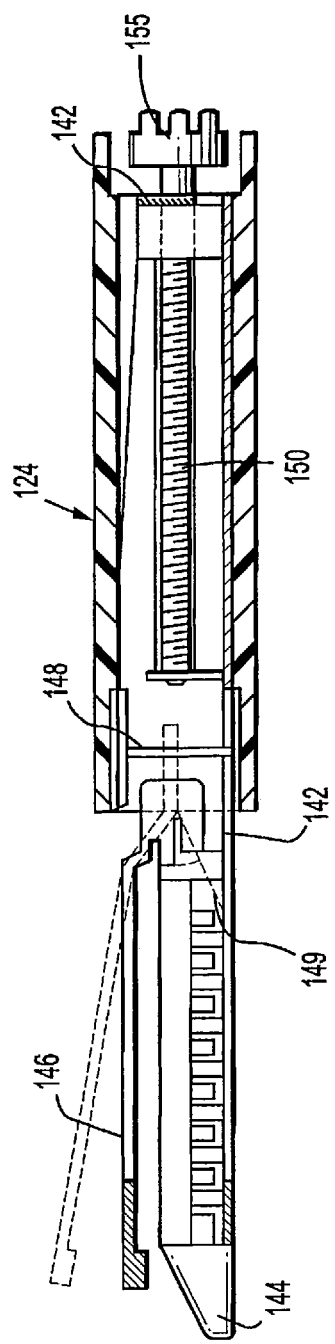
FIG. 7A-C are cross-sectional side views of the stapling assembly of FIG. 6 in a first or open position (A), a second, partially actuated position (B), and in a third, fully actuated position (C)
Figure 7B:
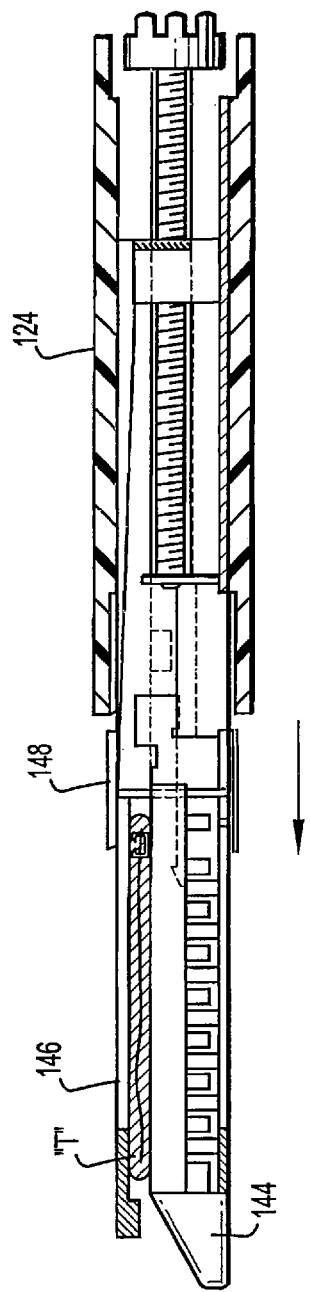
Figure 7C:
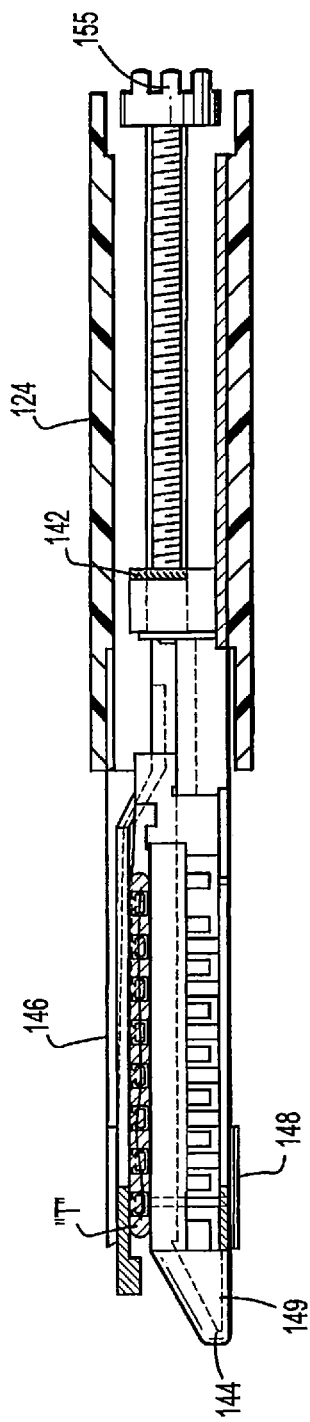

Briefly, and with reference to FIGS. 6-7c, tool assembly 140 includes a base member 142, a staple cartridge 144, an anvil 146, a camming beam 148, camming bars 149, and a drive screw 150. Base member 142 extends from within articulating portion 124. Base member 142 is configured to receive staple cartridge 144 in the distal end thereof. Base member 142 is further configured for slideably receiving camming bars 149. Anvil 146 is configured to be positioned above staple cartridge 144 and to receive tissue "T" therebetween.

Drive screw 150 is rotatably mounted within base 142 and articulation portion 124. Proximal end 150a of drive screw 150 include a second articulation gear 155 configured for engagement with first articulation gear 125. Distal end 150b of drive screw 150 includes a threaded portion for receiving a support member 152. Support member 152 is configured to longitudinally traverse threaded portion 150b of drive screw 150 upon rotation thereof. Rotation of drive screw 150 in a first direction causes support member 152 to distally traverse screw 150, while rotation in a second direction causes proximal movement of support member 152.

Camming beam 148 and camming bars 149 are configured such that as support member 152 traverses distally beam 148 and bars 149 also traverse distally. Camming beam 148 is configured to engage staple cartridge 144 and anvil 146 as drive screw 150 rotates in a first direction and distally advances support member 152 (FIGS. 7B and 7C). At the same time camming bars 149 interact with staple pushers 153 to eject staples from cartridge assembly 144. Rotation of drive screw 150 in a second direction proximally retracts support member 152, thereby disengaging camming beam 148 from staple cartridge 144 and anvil 146.

In operation, endoscopic portion 120 of surgical stapler 100 is inserted through a cannula or other opening in the body. Once endoscopic portion 120 is positioned within the body cavity, tool assembly 140 mounted on the distal end of articulation portion 124 may be manipulated into position using rotation knob 121 and articulation knob 128. As described above, rotation knob 121 may rotate tool assembly 140 three-hundred and sixty degrees (360°) relative to handle assembly 110, and because of the configuration of articulation joint 130, proximal movement of articulation knob 128 may articulate endoscopic portion 120 to any angle up to, and including, ninety degrees (90°). Tool assembly 140 may be actuated at any and all angles up to and including 90°. Tool assembly 140 may be actuated as articulation joint 130 is articulated.

Figure 8A:
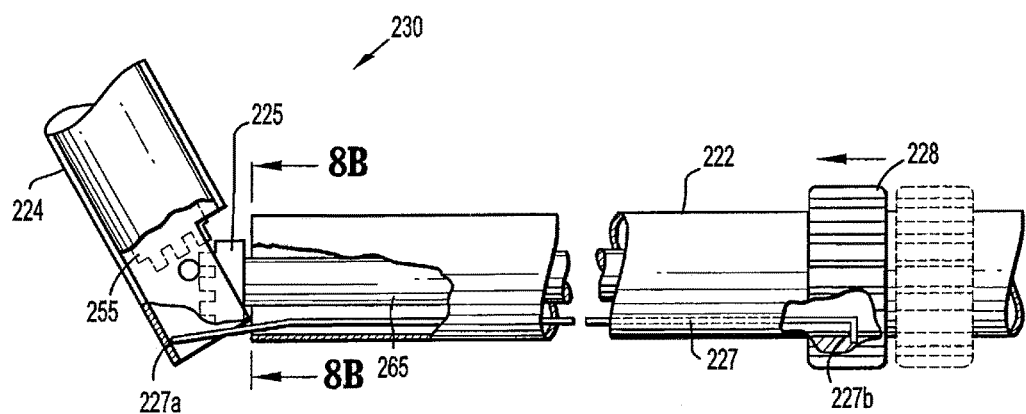
FIG. 8A is a partial cut away top view of an articulating shaft according to an alternate embodiment of the present disclosure.
Figure 8B:
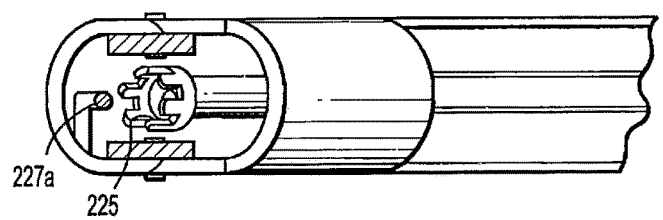
FIG. 8B is a cross-sectional view taken along section line 8B-8B of FIG. 8A.

Referring now to FIGS. 8A and 8B, an alternate embodiment of the present disclosure is shown generally as articulation joint 230. Articulation joint 230 is substantially similar to articulation joint 130. Articulation joint 230 includes elongated portion 222, articulation portion 224 and articulation rod 227. Proximal end 227b of articulation rod 227 is secured to articulation knob 228. Distal end 227a of articulation rod 227 forms a hook for securely engaging articulation portion 224. Movement of articulation knob 228 in a distal direction causes articulation of articulation joint 230. Return of articulation knob 228 to its original position causes the straightening of articulation joint 230.

In further embodiments, the camming bars 149 are replaced with a sled having one or more cam wedges integrally formed. The advancement of the camming beam 148 drives the sled forwardly through the staple cartridge 144. The length of the camming beam 148 may be shortened. The sled may be as disclosed in commonly owned U.S. Pat. No. 5,865,361 to Milliman, et al., the disclosure of which is hereby incorporated by reference herein in its entirety. In the '361 patent, actuation sled 234 is shown in FIG. 21.

In further embodiments, a motorized handle assembly is used to rotate drive shaft 65. The motorized handle assembly may be as described in U.S. patent application Ser. No. 11/786,934, filed Apr. 13, 2007, entitled "Power Surgical Instrument," the disclosure of which is hereby incorporated by reference herein in its entirety.

It will be understood that various modifications may be made to the embodiments disclosed herein. For example, the components of the surgical apparatus can be formed of any material suitable for surgical use and having the required strength characteristics. Therefore, the above description should not be construed as limiting, but merely as exemplifications of the disclosed embodiments. Those skilled in the art will envision other modifications within the scope and spirit of the claims appended hereto.

What is claimed is:

1. A surgical apparatus comprising:
a handle assembly;
an elongated body extending from the handle assembly and including a proximal portion, a distal portion, and an articulation joint disposed between the proximal portion and the distal portion;
an articulation mechanism disposed within the elongated body configured to move the distal portion about the articulation joint from a first position in axial alignment with the proximal portion to a second position offset from the proximal portion; and
a drive assembly extending through the elongated body, the drive assembly including a first drive shaft extending from the handle assembly to the articulation joint and a second drive shaft extending from the articulation joint to a tool assembly, wherein the first drive shaft includes an extension mechanism for maintaining the first drive shaft in direct engagement with the second drive shaft during articulation of the distal portion of the elongated body about the articulation joint, and rotation of the first drive shaft in relation to a longitudinal axis of the proximal portion of the elongated body in a first direction causes rotation of the second drive shaft in the first direction in relation to a longitudinal axis of the distal portion of the elongated body when the distal portion is in any of the first or second positions.

2. The surgical apparatus of claim 1, wherein the extension mechanism is configured to extend and contract a length of the first drive shaft.

3. The surgical apparatus of claim 1, wherein the extension mechanism includes a receiving end slidably disposed relative to an insertion end.

4. The surgical apparatus of claim 3, wherein the extension mechanism further includes a spring disposed between the receiving end and the insertion end configured to bias the receiving end distally.

5. The surgical apparatus of claim 3, wherein the receiving end includes a raised portion configured for engagement with a groove defined by the insertion end.

6. The surgical apparatus of claim 1, wherein the first drive shaft includes a first gear having a first plurality of teeth.

7. The surgical apparatus of claim 6, wherein the second drive shaft includes a second gear having a second plurality of teeth.

8. The surgical apparatus of claim 7, wherein the extension mechanism is configured to maintain at least one of the first plurality of teeth of the first gear in engagement with at least one of the second plurality of teeth of the second gear during articulation of the distal portion of the elongated body about the articulation joint.

9. The surgical apparatus of claim 1, further comprising a tool assembly including one of a clip applier, vessel sealer, and forceps.

10. The surgical apparatus of claim 1, further comprising a tool assembly including a stapling assembly.

11. The surgical apparatus of claim 1, wherein the handle assembly includes an actuation mechanism including a movable handle and a gear attached to the first drive shaft configured to rotate the first drive shaft.

12. The surgical stapler of claim 1, wherein rotation of the first drive shaft in relation to the longitudinal axis of the proximal portion of the elongated body in a clockwise direction cause rotation of the second drive shaft in relation to the longitudinal axis of the distal portion of the elongated body in a clockwise direction.

13. The surgical stapler of claim 1, wherein in the first direction is clockwise.

14. A surgical apparatus comprising:
   a handle assembly;
   an elongated body extending from the handle assembly and including a proximal portion, a distal portion, and an articulation joint disposed between the proximal portion and the distal portion, the proximal portion defining a first longitudinal axis and the distal portion defining a second longitudinal axis;
   an articulation mechanism disposed within the elongated body configured to move the distal portion about the articulation joint from a first position in axial alignment with the proximal portion to a second position offset from the proximal portion; and
   a drive assembly extending through the elongated body, the drive assembly including a first drive shaft extending from the handle assembly to the articulation joint and a second drive shaft extending from the articulation joint to a tool assembly, wherein the first drive shaft includes an extension mechanism for maintaining the first drive shaft in direct engagement with the second drive shaft during articulation of the distal portion of the elongated body about the articulation joint, and rotation of the first drive shaft in a first direction relative to the first longitudinal axis causes rotation of the second drive shaft relative to the second longitudinal axis in the first direction when the distal portion is in the second position.

15. The surgical apparatus of claim 14, wherein the extension mechanism is configured to extend and contract a length of the first drive shaft.

16. The surgical apparatus of claim 14, wherein the extension mechanism includes a receiving end slidably disposed relative to an insertion end.

17. The surgical apparatus of claim 16, wherein the extension mechanism further includes a spring disposed between the receiving end and the insertion end configured to bias the receiving end distally.

18. The surgical apparatus of claim 16, wherein the receiving end includes a raised portion configured for engagement with a groove defined by the insertion end.

19. The surgical apparatus of claim 14, wherein the first drive shaft includes a first gear having a first plurality of teeth.

20. The surgical apparatus of claim 19, wherein the second drive shaft includes a second gear having a second plurality of teeth.

21. The surgical apparatus of claim 20, wherein the extension mechanism is configured to maintain at least one of the first plurality of teeth of the first gear in engagement with at least one of the second plurality of teeth of the second gear during articulation of the distal portion of the elongated body about the articulation joint.

* * * * *